United States Patent [19]
Gronvall

[11] Patent Number: 5,810,724
[45] Date of Patent: Sep. 22, 1998

[54] REUSABLE SENSOR ACCESSORY CONTAINING A CONFORMABLE SPRING ACTIVATED RUBBER SLEEVED CLIP

[75] Inventor: Daniel Gronvall, Pleasanton, Calif.

[73] Assignee: Nellcor Puritan Bennett Incorporated, Pleasanton, Calif.

[21] Appl. No.: 566,306

[22] Filed: Dec. 1, 1995

[51] Int. Cl.$^6$ .................................................. A61B 5/00
[52] U.S. Cl. ..................... 600/323; 600/310; 600/322; 600/340; 600/344
[58] Field of Search ............................... 128/633, 664–7; 24/489, 490, 499, 500, 501, 504; 600/310, 314–316, 322–324, 326, 328, 340, 344

[56] References Cited

U.S. PATENT DOCUMENTS

| | | | |
|---|---|---|---|
| D. 250,275 | 11/1978 | Bond | D24/29 |
| 847,106 | 3/1907 | Pasqualin | 24/500 |
| 1,468,884 | 9/1923 | Schneider | 24/500 |
| 1,531,680 | 5/1925 | Stenersen | 24/500 |
| 3,152,587 | 10/1964 | Ullrich et al. | 128/2 |
| 3,810,460 | 5/1974 | Van Nie | 128/2.05 |
| 4,321,930 | 3/1982 | Jöbsis et al. | 128/633 |
| 4,334,544 | 6/1982 | Hill et al. | 128/644 |
| 4,510,938 | 4/1985 | Jöbsis et al. | 128/633 |
| 4,685,464 | 8/1987 | Goldberger et al. | 128/633 |
| 4,825,872 | 5/1989 | Tan et al. | 128/633 |
| 4,825,879 | 5/1989 | Tan et al. | 128/633 |
| 4,830,014 | 5/1989 | Goodman et al. | 128/665 |
| 4,913,150 | 4/1990 | Cheung et al. | 128/633 |
| 4,915,116 | 4/1990 | Hasebe et al. | 128/666 |
| 4,974,591 | 12/1990 | Awazu et al. | 128/633 |
| 5,035,243 | 7/1991 | Muz | 128/633 |
| 5,054,488 | 10/1991 | Muz | 128/633 |
| 5,090,410 | 2/1992 | Saper et al. | 128/633 |
| 5,209,230 | 5/1993 | Swedlow et al. | 128/633 |
| 5,217,012 | 6/1993 | Young et al. | 128/633 |
| 5,247,931 | 9/1993 | Norwood | 128/633 |
| 5,313,940 | 5/1994 | Fuse et al. | 128/633 |
| 5,339,810 | 8/1994 | Ivers et al. | 128/633 |
| 5,361,757 | 11/1994 | Smith et al. | 128/633 |
| 5,368,025 | 11/1994 | Young et al. | 128/633 |
| 5,390,670 | 2/1995 | Centa et al. | 128/633 |
| 5,413,099 | 5/1995 | Schmidt et al. | 128/633 |
| 5,429,129 | 7/1995 | Lovejoy et al. | 128/633 |
| 5,619,992 | 4/1997 | Guthrie et al. | 128/633 |

FOREIGN PATENT DOCUMENTS

| | | |
|---|---|---|
| 41 42234A1 | 6/1993 | Germany . |
| WO 96/00518 | 6/1995 | WIPO . |

OTHER PUBLICATIONS

Product Literature of BCI International, re: "OxiLink".

*Primary Examiner*—Jennifer Bahr
*Assistant Examiner*—Bryan K. Yarnell
*Attorney, Agent, or Firm*—Townsend and Townsend and Crew LLP

[57] ABSTRACT

A reusable accessory for a sensor (such as a pulse oximeter or a plethysmograph) that allows close conformance between the sensor heads and the patient tissue to be measured. The accessory thus provides both a key advantage of adherent sensors (i.e. close tissue-sensor conformance) and a key advantage of rigid structure sensors (reusability). The accessory provides a structure for mounting the sensor heads, whereby the sensor heads can pivot about their respective points of attachment to the mounting structure within first and second voids, respectively, thereby allowing the sensors to closely conform to the patient tissue. In one embodiment, the mounting structure includes a spring containing two coils, and two frames surrounding the voids and connected to the coils, each frame having an end shaped to fit a portion of a sensor head and onto which a sensor head is mounted. Another aspect of the present invention, concerns the use of flexible sleeves to cover the sensor heads when mounted on a reusable accessory. The sleeves can be replaced or cleaned between patient applications, thereby reducing the risk of cross contamination between patients, and reduce the amount of shunted light. Yet another aspect of the present invention involves sensory accessories providing light shields that reduce shunting for non-flat site applications and yet do not interfere with sensor-tissue conformance in flat site applications.

6 Claims, 11 Drawing Sheets

FIG. 12

REUSABLE SENSOR ACCESSORY CONTAINING A CONFORMABLE SPRING ACTIVATED RUBBER SLEEVED CLIP

BACKGROUND OF THE INVENTION

This invention relates to sensors for use with non-invasive pulse monitors such as plethysmographs or pulse oximeters.

A plethysmograph is a pulse monitor. The plethysomograph sensor shines light into the patient's tissue, and the light transmitted through the tissue is received by a photodetector. The photodetector generates electrical signals corresponding to the transmitted light levels and transmits the signals to a monitor for processing. Arterial blood will absorb some of the light, with more light being absorbed when there is more blood. Thus, changes in the amount of transmitted light are related to pulses of arterial blood in the illuminated tissue.

A pulse oximeter is a device for noninvasively determining the oxygen saturation of arterial blood. The pulse oximeter sensor shines light at two different wavelengths (one in the red range, the other in the infrared range) through a portion of the patient's blood-perfused tissue. The red and infrared light scattered by through the tissue is detected by a photodetector. The amount of light absorbed varies with the amount of oxygen in the blood, and varies differently for red and infrared light. The pulse oximeter monitor computes blood oxygen saturation based on the changes in the two detected light levels between two points in time.

A key issue regarding the performance of the above discussed sensors is the degree to which the surface of the sensor conforms to the surface of the tissue being measured. Poor sensor-tissue conformance provides a path for ambient light to reach the photodetector and to thereby distort the measurements of the sensor. In addition, poor sensor-tissue conformance interferes with retention of the light generated by the transmitter and facilitates shunting (i.e. the transmission of light from the transmitter to the detector via a path not going through the tissue to be measured) as well as relative motion between the sensor and tissue, all of which phenomena can distort the measurements of the sensor.

One type of sensor providing excellent sensor-tissue conformance is sometimes referred to as an "adherent sensor". U.S. Pat. No. 4,830,014 describes one such sensor, having a flexible web onto which a transmitter and detector are mounted. The web has an adhesive surface for attachment to a patient tissue, thereby permitting close sensor-tissue conformance. Adherent sensors, however, are typically restricted to one application due in part to a decrease in adhesive effectiveness with each application and in part to the difficulties in cleaning and sterilization for reuse. Thus, the use of adherent sensors can make pulse oximetry expensive.

On the other hand, many reusable sensors tend to employ rigid structures (such as two legs of a clip or clothes-pin type arrangement, for ex. see U.S. Pat. Nos. 3,152,587 and 3,810,460) for housing the detector and transmitter and as a result often conform poorly to a patient tissue. U.S. Pat. No. 4,685,464 discloses a similar type rigid structure with deformable pads which facilitate tissue-sensor conformance. However, the sensor heads (i.e. detector and transmitter) in this sensor are permanently embedded in the rigid structure. A recent trend in sensors involves the use of sensor heads that can be removably attached to a variety of sensor accessories (each of which is tailored to different applications, e.g. for attachment to an ear, finger etc.), thereby rendering pulse oximetry over many different tissue sites less expensive. One such sensor is sold under the name "Y-sensor" by Nellcor Incorporated of Pleasanton, Calif. (the assignee of the present application) and depicted by reference numeral 201 of FIG. 2.

What is needed is a reusable sensor with removably attachable sensor heads that is capable of providing a high degree of tissue-sensor conformance.

SUMMARY OF THE INVENTION

The present invention provides a reusable accessory for a sensor (such as a pulse oximeter or a plethysmograph) that allows close conformance between the sensor heads and the patient tissue to be measured. The accessory thus provides both a key advantage of adherent sensors (i.e. close tissue-sensor conformance) and a key advantage of rigid structure sensors (reusability). The accessory provides a structure for mounting the sensor heads, whereby the sensor heads can pivot about their respective points of attachment to the mounting structure within first and second voids, respectively, thereby allowing the sensors to closely conform to the patient tissue. Sensor accessories for other applications (e.g. for attachment to an ear) could be modified to provide a similar mounting structure and resulting close tissue-sensor conformance.

In one embodiment, the mounting structure includes a spring containing two coils, and two frames connected to the coils, each frame having an end shaped to fit a portion of a sensor head and onto which a sensor head is mounted. When mounted on the frames, the sensor heads can pivot within voids located inside the frames. In another embodiment, the structure for mounting includes a stamped spring having two ends, each of which is shaped to fit a portion of a sensor head. In another embodiment, the structure for mounting includes two stamping forms, each of the stamping forms having an end shaped to fit a portion of one of the sensor heads.

Another aspect of the present invention concerns the use of flexible sleeves to cover the sensor heads when mounted on a reusable sensor accessory. Such flexible sleeves can be used in conjunction with the mounting structures described immediately above (which permit the sensor heads to pivot) and with prior art mounting structures (not permitting the sensor heads to pivot). The sleeves can be replaced or cleaned between patient applications, thereby reducing the risk of cross contamination between patients. In addition, the sleeves can be colored and shaped to reduce the amount of shunting (i.e. light that travels from one sensor head to the other without passing through the patient tissue). Also, the use of a variety of sleeves with different shapes may enable the same mounting structure to conform to a variety of tissue sites and patient types.

Yet another aspect of the present invention concerns sensory accessories providing light shields that reduce shunting in non-flat site applications but yet do not interfere with tissue-sensor conformance in flat site applications (such as where the tissue site is the web between the thumb and forefinger). In one embodiment, such an accessory contains two frames in each of which a sensor head is mounted, as well as light shields attached to the sides of the frames. The shields can be in one of two positions: coplanar with the frames (for flat site applications) and rotated to be perpendicular to the frames (for non-flat site applications). In another embodiment, the sensor accessory contains two frames in each of which a sensor head is mounted, and two flexible sleeves for covering the two frames. The flexible sleeves have sides that act as light shields in non-flat site applications but flatten under pressure in flat site applications, thereby permitting close conformance between the sensor and flat sites. In yet another embodiment, the sensor accessory consists of two wire frames that can fold to surround a non-flat site. Each of the wire frames is covered by a flexible sleeve. When the wire frames are folded to surround a non-flat site, the flexible sleeves act as light shields.

DESCRIPTION OF THE PREFERRED EMBODIMENT

Figure 2:
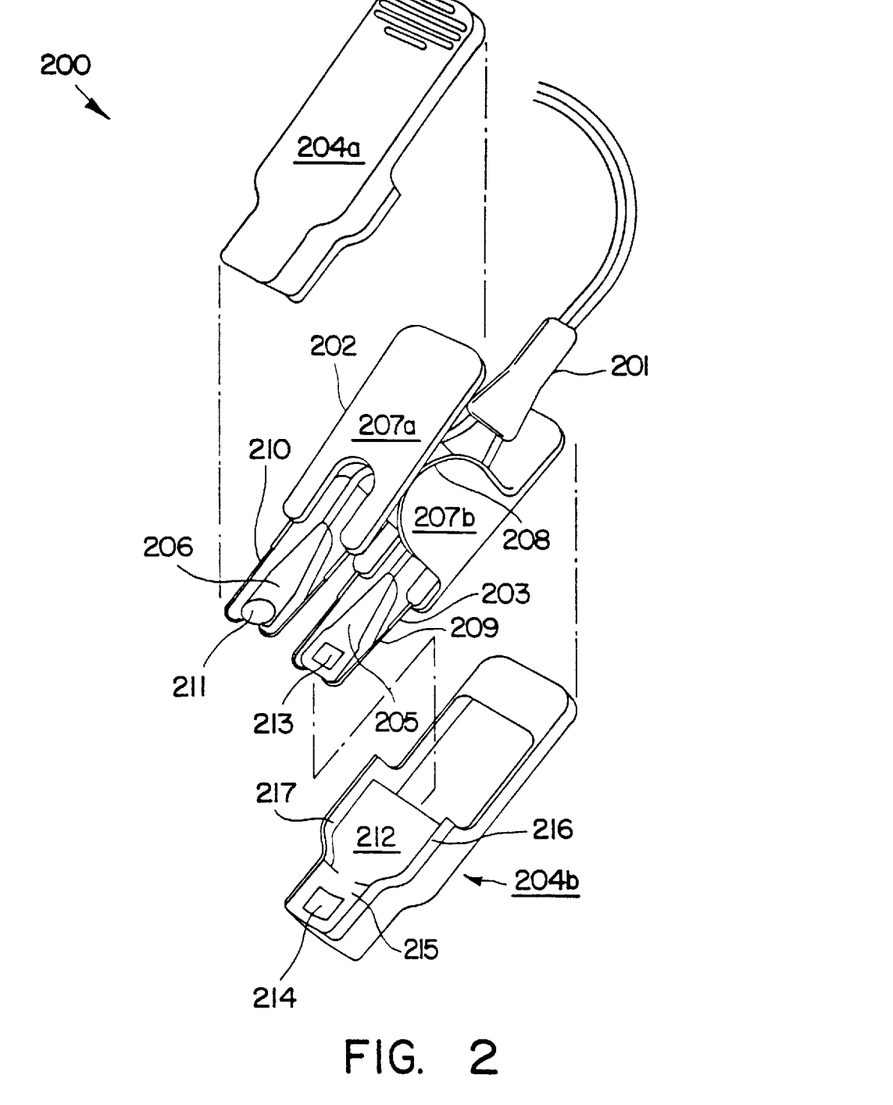
FIG. 2 is an exploded view of a partially assembled sensor using an accessory permitting the sensor heads to pivot.

FIG. 2 illustrates a partially assembled oximeter 200 according to the present invention. Oximeter 200 consists of a sensor 201, a spring activated clip 202, a spring 203 and rubber sleeves 204a and 204b (the latter four items are hereinafter referred to as a "sensory accessory"). (In alternate embodiments, sleeves 204a and 204b could be made of a flexible material other than rubber.) Sensor 201 contains a phototransmitter 205 and a photodetector 206 (each of the latter two items is sometimes referred to as a "sensor head"). Clip 202 contains an upper portion 207a and a lower portion 207b, which are illustrated in more detail in FIGS. 6 and 7, respectively. Spring 203, which is illustrated in more detail in FIG. 5, contains a left spring coil 208, a corresponding right spring coil (indicated by reference numeral 703 in FIG. 5), a lower spring frame 209 and an upper spring frame 210.

In order to assemble oximeter 200, transmitter 205 and detector 206 are pulled through a cavity between clip upper portion 207a and clip lower portion 207b. A button-shaped portion 211 of detector 206 and a similar button-shaped portion (not shown) of phototransmitter 205 are then mounted into ends (identified in FIG. 5 by reference numerals 701 and 702, respectively) of upper and lower spring frames 210 and 209, respectively. When so mounted, detector 206 and transmitter 205 rest within voids 704 and 705, respectively. Ideally, the cavity between clip portions 207a and 207b is sufficiently small so as to prevent transmitter 205 and detector 206 from slipping backwards through the cavity (i.e. away from spring frames 209 and 210.) if the grip on transmitter 205 and detector 206 is lost while attempting to perform this last fitting step.

Finally, sleeve 204b is placed over lower spring frame 209 and the flat part of clip lower portion 207b (i.e. the part coplanar with lower spring frame 209). Lower spring frame 209 and transmitter 205 are placed inside sleeve 204b underneath a flap portion 212 of sleeve 204b, in such a way so as to align a window 213 of transmitter 205 with a window 214 of sleeve 204b. Sleeve 204a is similarly placed over upper spring frame 210 and the flat part of clip upper portion 207a, in such a way so as to align a window (not shown) of detector 206 with windows 213 and 214 and a window (not shown) of sleeve 204a. Except for their respective windows, sleeves 204a–b are largely opaque to the light transmitted by transmitter 205 (i.e. the amount of light transmitted through sleeves 204a–b is comparable to the amount of light picked up by detector 206 from noise sources). The above-mentioned windows should be thin, so as to limit the attenuation of the light transmitted from transmitter 205 to detector 206. Window 214 of sleeve 204b and the corresponding window of sleeve 204a should be shaped to closely match the respective shapes of transmitter 205 and detector 206, respectively.

Figure 1:
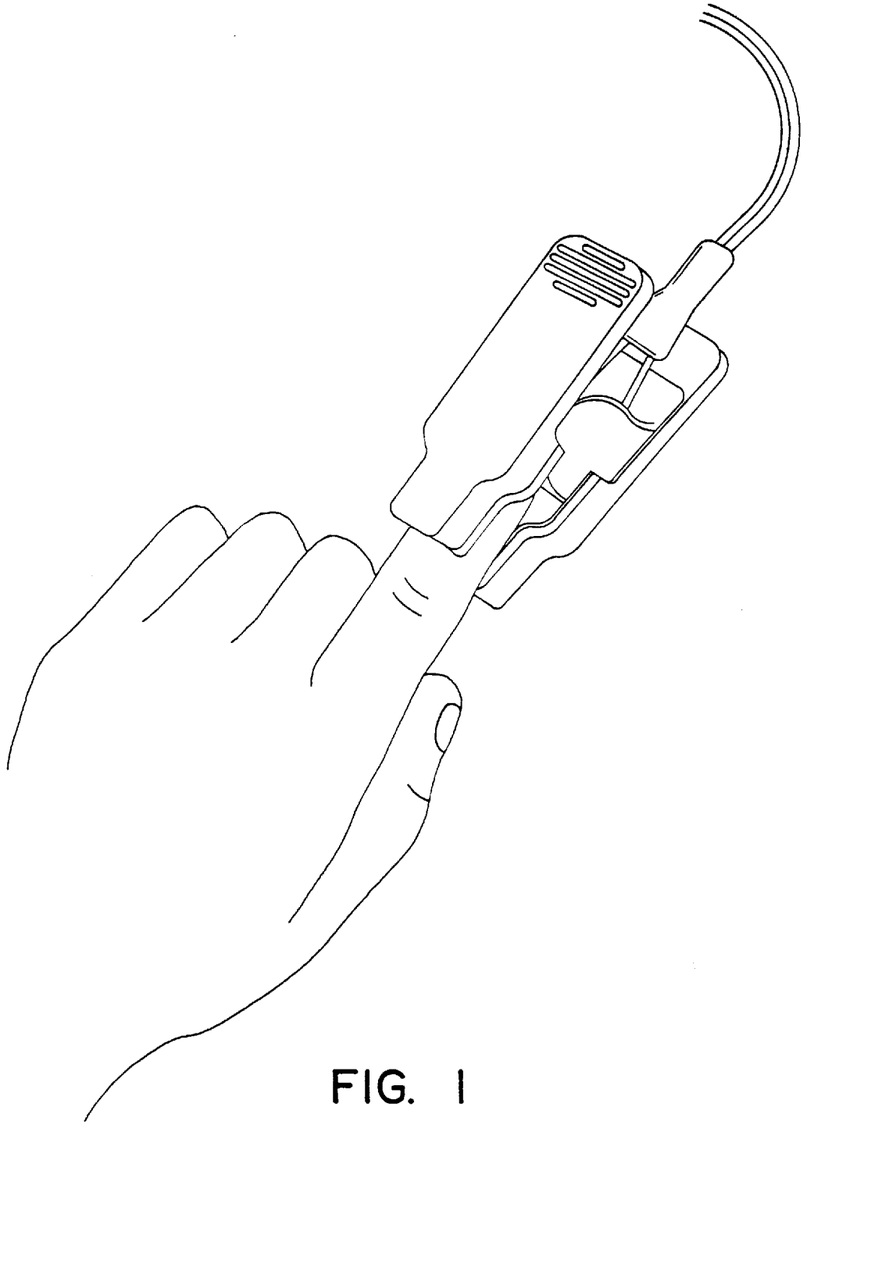
FIG. 1 is a diagram illustrating the application to a patient of the sensor accessory of FIG. 2.

Once oximeter 200 is assembled, the ends of upper and lower clip portions 207a–b are pressed together, thereby separating lower and upper spring frames 209 and 210 and permitting the patient's tissue to rest between a pad portion 215 of sleeve 204b and a corresponding pad portion (not shown) of sleeve 204a. Edge portions 216–217 of sleeve 204b flank pad portion 215 and, along with corresponding edge portions of sleeve 204a (not shown), should be of sufficient thickness so as to inhibit the rotation of oximeter 200 about the measured tissue at an angle perpendicular to edge portions 216–217. Upon release of upper and lower clip portions 207a–b, the tissue is held tightly in place, as illustrated in FIG. 1. In one embodiment, peel-off adhesives could be placed on pad portion 215 and the corresponding pad portion of sleeve 204a to minimize the problem of relative motion between the patient tissue and the sensor heads.

Upper clip portion 207a contains two cylinders 6002 and 6003 (FIG. 6), each defining a hollow in which a respective one of discs 7001 and 7003 (FIG. 7) of lower clip portion 207b rotates to separate or bring together lower and upper frame portions 209–210. A wedge shaped hollow 7002 is cut out of disc 7001. A similarly shaped hollow (not shown) is cut out of disc 7003. A wedge shaped piece 6001 is positioned inside the hollow defined by cylinder 6002. A similarly shaped piece (not shown) is positioned inside the hollow defined by cylinder 6003. When discs 7001 and 7003 are positioned within the hollows defined by cylinders 6003 and 6002, respectively, the wedge shaped pieces inside cylinders 6003 and 6002 sit within the wedge shaped hollows cut out of disc 7001 and 7003, respectively.

Figure 6:
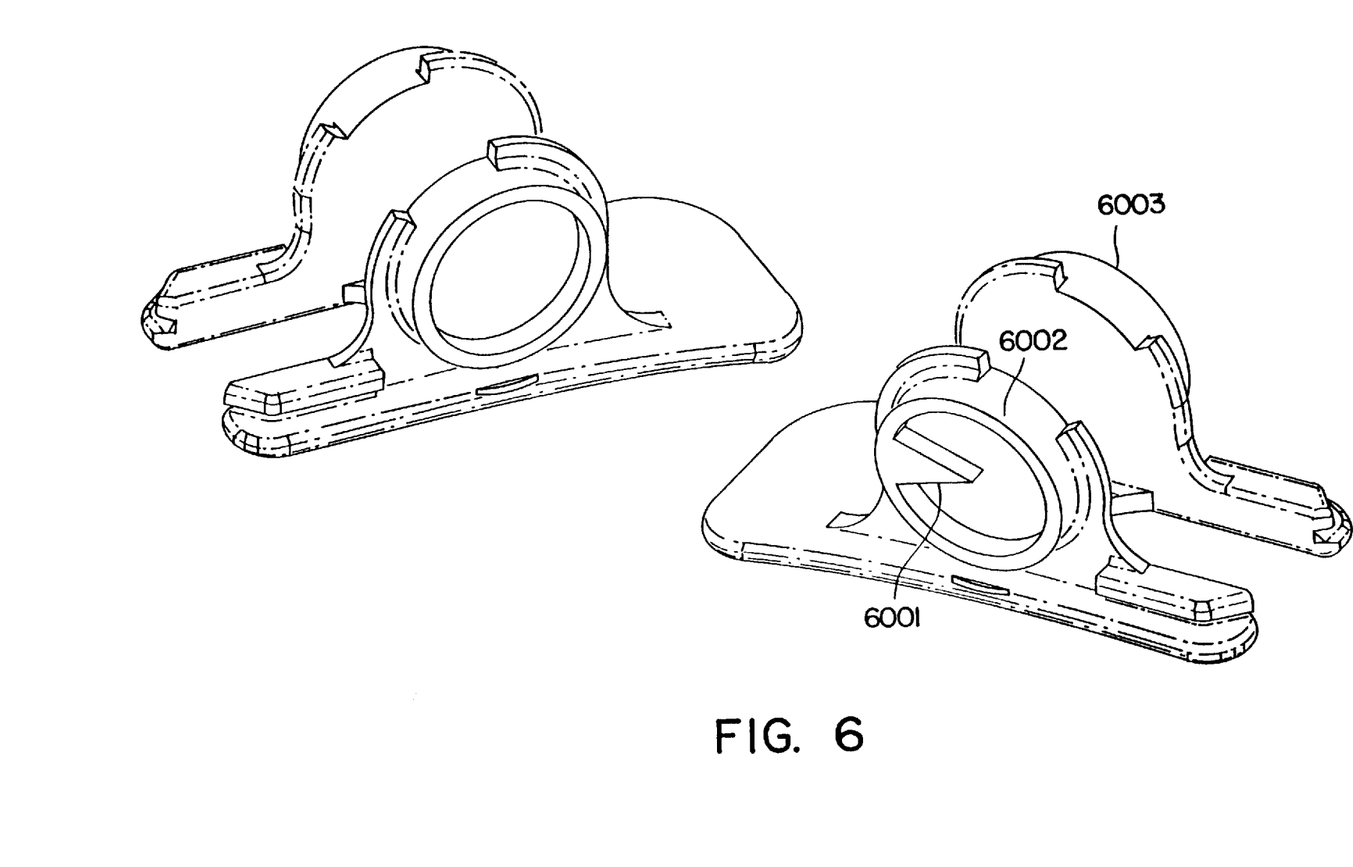
FIG. 6 is a diagram illustrating upper clip portion 207a of the sensor accessory of FIG. 2.
Figure 7:
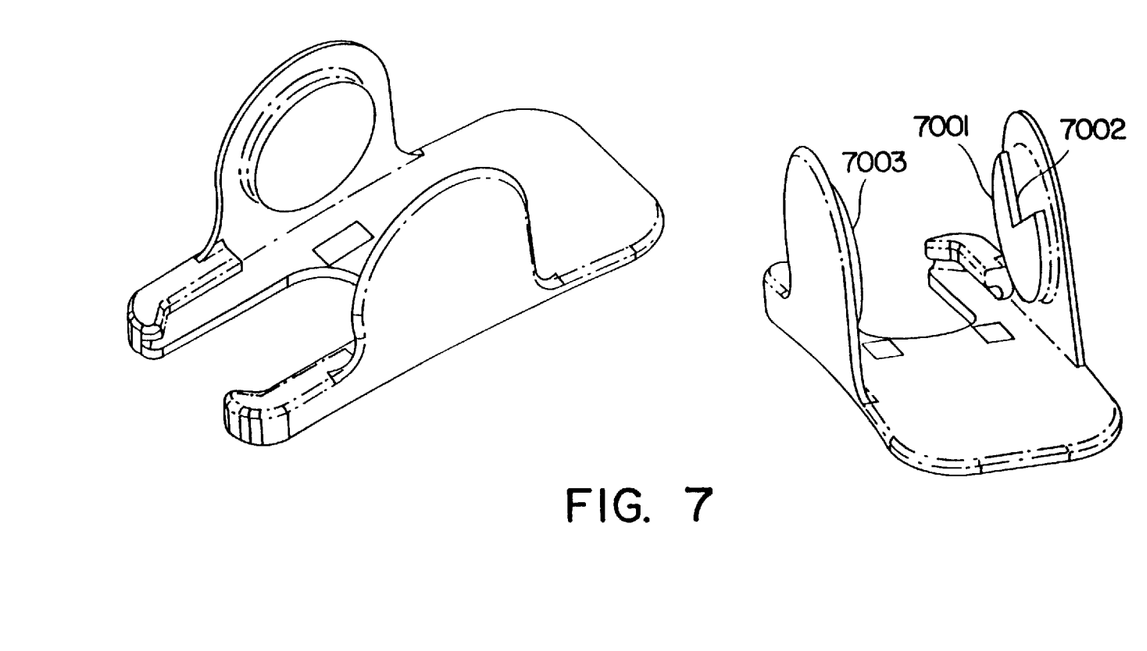
FIG. 7 is a diagram illustrating lower clip portion 207b of the sensor accessory of FIG. 2.

Thus, the degree to which disc 7001 and 7003 can rotate within cylinders 6003 and 6002, respectively, is limited in both the clockwise and counterclockwise directions. As a result, the degrees to which lower and upper frame portions 209–210 can be brought together and separated, respectively, are limited. The limitation on the degree to which frame portions 209–210 can be brought together may prevent sleeves 204a–b from deforming under continuous pressured contact when the accessory of FIG. 2 is not being used.

Figure 5:
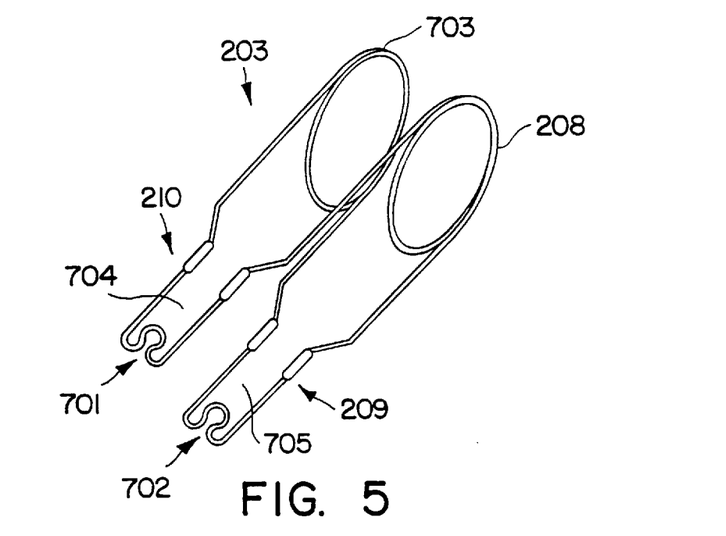
FIG. 5 is a diagram illustrating the spring component 203 of the accessory of FIG. 2

A key advantage of the sensory accessory used in oximeter 200 is the ability of detector 206 and transmitter 205 to pivot up and down within voids 704 and 705, respectively, about their point of attachment to ends 701 and 702 of upper and lower frame portions 210 and 209, respectively. This pivoting ability permits detector 206 and transmitter 205 to conform to a greater degree to the tissue to be measured (particularly irregular surfaces) over a broad range of patients and different tissue sites, than is typically possible with prior art oximeters in which the detector and transmitter are embedded in a rigid structure accessory. This closer sensor to tissue conformance results in less ambient light reaching the detector and thus more accurate readings. Flap portion 212 of sleeve 204b and the corresponding flap portion (not shown) of sleeve 204a should be sufficiently thin so as to not interfere with the range of pivoting motion of detector 206 and transmitter 205.

Figure 3:
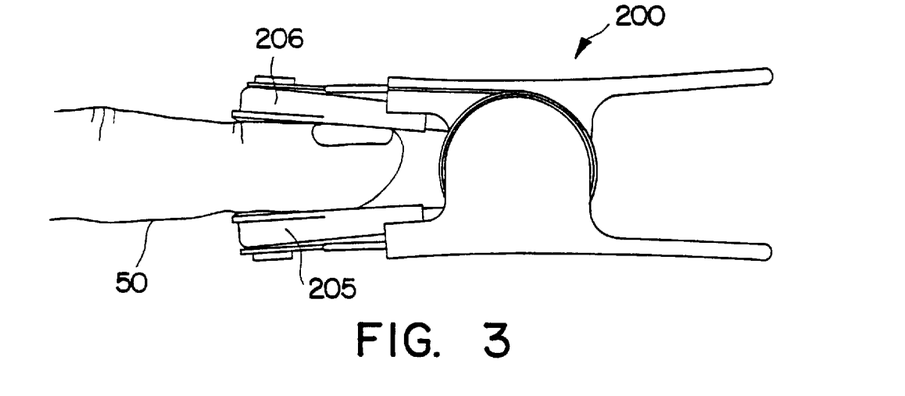
FIG. 3 is a diagram illustrating the close tissue-sensor conformance realized with the sensor accessory of FIG. 2.
Figure 4:
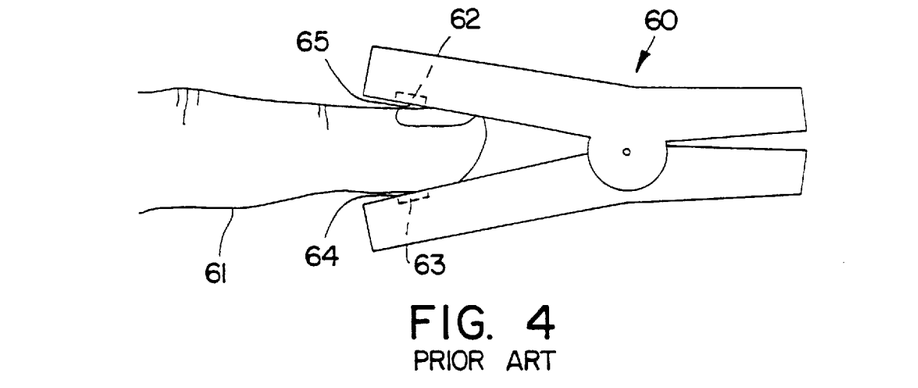
FIG. 4 is a diagram illustrating gaps between the tissue and the sensor heads that can occur when using a prior art rigid structure sensor accessory.

For example, FIG. 3 illustrates a tissue 50 in place to be measured by oximeter 200. As shown, the pivoting ability described above permits detector 206 and transmitter 205 to conform closely to tissue 50, thereby reducing the problem of ambient light. By contrast, FIG. 4 illustrates a rigid structure oximeter 60. A tissue 61 determines the angle at which the clip of oximeter 60 is opened. This angle determines the angles at which a detector 62 and a transmitter 63, both of which are embedded in oximeter 60, meet tissue 61, and thereby results in gaps 65 and 63 between tissue 61 and detector 62 and between tissue 61 and transmitter 63, respectively. The presence of gaps 63 and 65 permits ambient light to distort the readings of oximeter 60.

The sensor accessory of FIG. 2 provides a new use for the existing "Y-sensor", described above, in applications similar to those suited to the rigid clothes-pin structure sensor of U.S. Pat. No. 4,685,464 (in which the sensor heads are permanently embedded). Existing sensor accessories for other applications (e.g. for attachment to an ear) could be modified to include a mounting structure for the sensor heads similar to spring 203.

Rubber sleeves 204a–b provide several advantages including the following:

1) Due to their opacity, sleeves 204a–b act as light shields and thereby reduce shunting, i.e. the amount of light from transmitter 205 that reaches detector 206 through an undesired path (i.e. not through the tissue whose oxygen level is to be measured).

2) Sleeves 204a–b, which can be cleaned or replaced between applications, protect spring portions 209–210, detector 206 and transmitter 205 from contamination which could distort readings of oximeter 200 and result in cross-contamination from one patient to another. Ideally, sleeves 204a–b have no gaps or crevices, which could shelter contaminants during cleaning.

3) Different sleeves can be used to achieve good sensor to tissue conformance for different tissue sites and/or for different patient shapes. For example, pad portion 215 of sleeve 204b (and the corresponding pad portion of sleeve 204a) should have a parabolic shape when oximeter 200 is used to measure the oxygen level in a child's finger. A sleeve with a differently shaped pad portion 215 might be appropriate for adults. A web-like structure in a sleeve might be appropriate for measuring the tissue between the thumb and forefinger.

The above advantages can also be obtained by using rubber sleeves in conjunction with prior art rigid structure sensor accessories in which the sensor heads cannot pivot.

Figure 8:
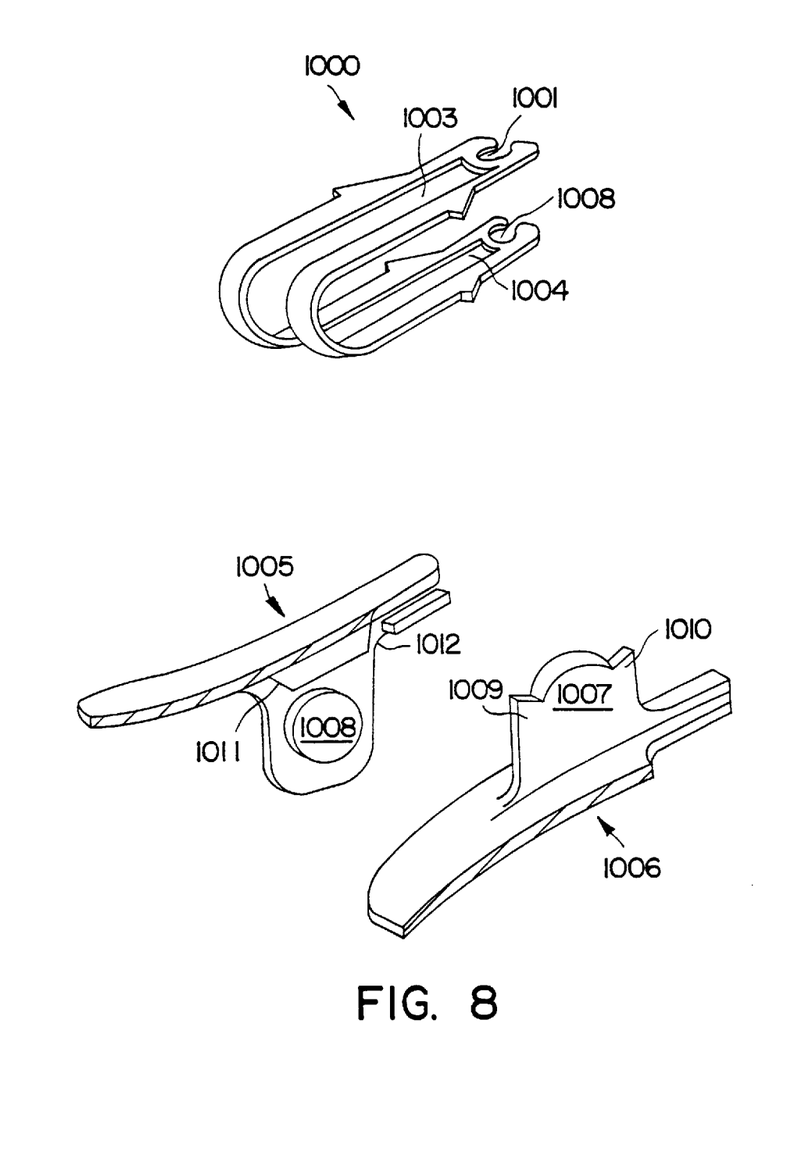
FIG. 8 is a diagram illustrating a sensory accessory containing a stamped spring.

FIG. 8 illustrates another type of sensor accessory that facilitates tissue-sensor conformance by allowing the detector and transmitter to pivot. The accessory comprises a stamped spring 1000, a top left clip/lever section 1005, a bottom left clip/lever section 1006 and corresponding top and bottom right clip/lever sections (not shown). The clip/lever sections are used to open stamped spring 1000 for tissue insertion.

The button shaped portions of transmitter 205 and detector 206 are mounted onto bottom and top ends 1002 and 1001 of stamped spring 1000, thereby permitting transmitter 205 and detector 206 to pivot within voids 1004 and 1003, respectively. Stamped spring 1000 is useful in applications requiring only a limited distance between the sensor heads (i.e. where the tissue is of limited thickness) so that the blending limits of spring 1000 are not exceeded.

When the sensory accessory of FIG. 8 is assembled, a circular portion 1007 of clip section 1006 is mounted onto a circular portion 1008 of clip section 1005. The abutment of a notch 1009 of clip section 1006 against a notch 1011 of clip section 1005 (similar notches are present on the top and bottom right clip/lever sections) limits the extent to which ends 1001–1002 of stamped spring 1000 can be separated. Similarly, the abutment of a notch 1010 of clip section 1006 against a notch 1012 of clip section 1005 (similar notches are present on the top and bottom right clip/lever sections) limits the extent to which ends 1001–1002 of stamped spring 1000 can be brought together. This latter limitation may prevent sleeves (not shown) placed on stamped spring 1000 over ends 1001 and 1002, from deforming under continuous pressured contact when the accessory of FIG. 8 is not being used.

Figure 9:
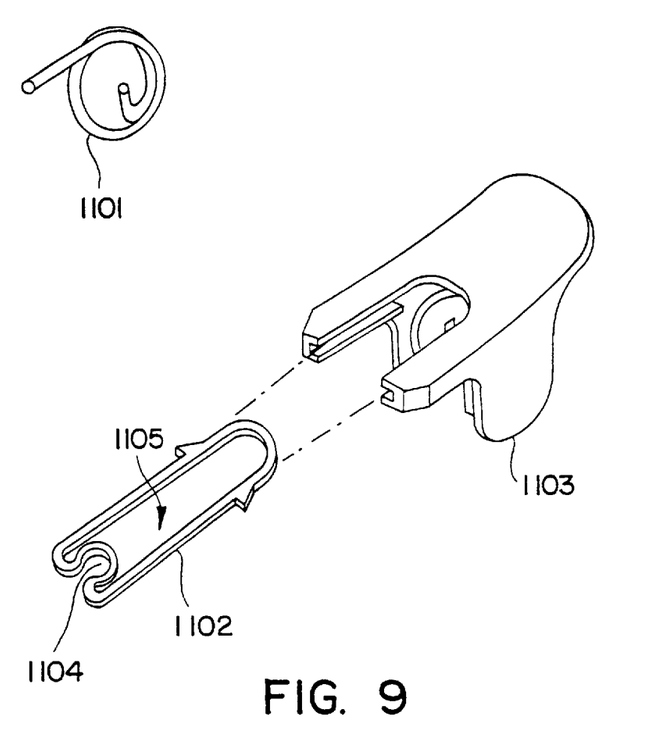
FIG. 9 is a diagram illustrating a sensory accessory containing a stamped form and a standard coil spring.

FIG. 9 illustrates yet another type of sensor accessory that facilitates tissue-sensor conformance by allowing the detector and transmitter to pivot. The sensor accessory of FIG. 9 is similar to that of FIG. 2, except that a standard commercially available coil spring 1101 (i.e. one without lower spring frame 209 and upper spring frame 210) is used instead of spring 203. An upper stamping form 1102 with an end 1104 is inserted into upper clip piece 1103. In one embodiment upper stamping form 1102 is made of wire. (In another embodiment stamping form 1102 is made of a glass-reinforced thermoplastic material, in which case stamping form 1102 and upper clip piece could be formed as one piece.) Button-shaped portion 211 of detector 206 is inserted into end 1104, thereby permitting detector 206 to pivot in void 1105. A similar lower stamping form (not shown) with an end similar to end 1104 (about which transmitter 205 pivots) is inserted into a lower clip piece (not shown). The upper and lower clip pieces of the accessory of FIG. 9 may contain features similar to those described above with reference to the accessory of FIG. 2 for limiting the degrees to which the upper and lower stamping forms can be brought together and separated, respectively.

Figure 10:
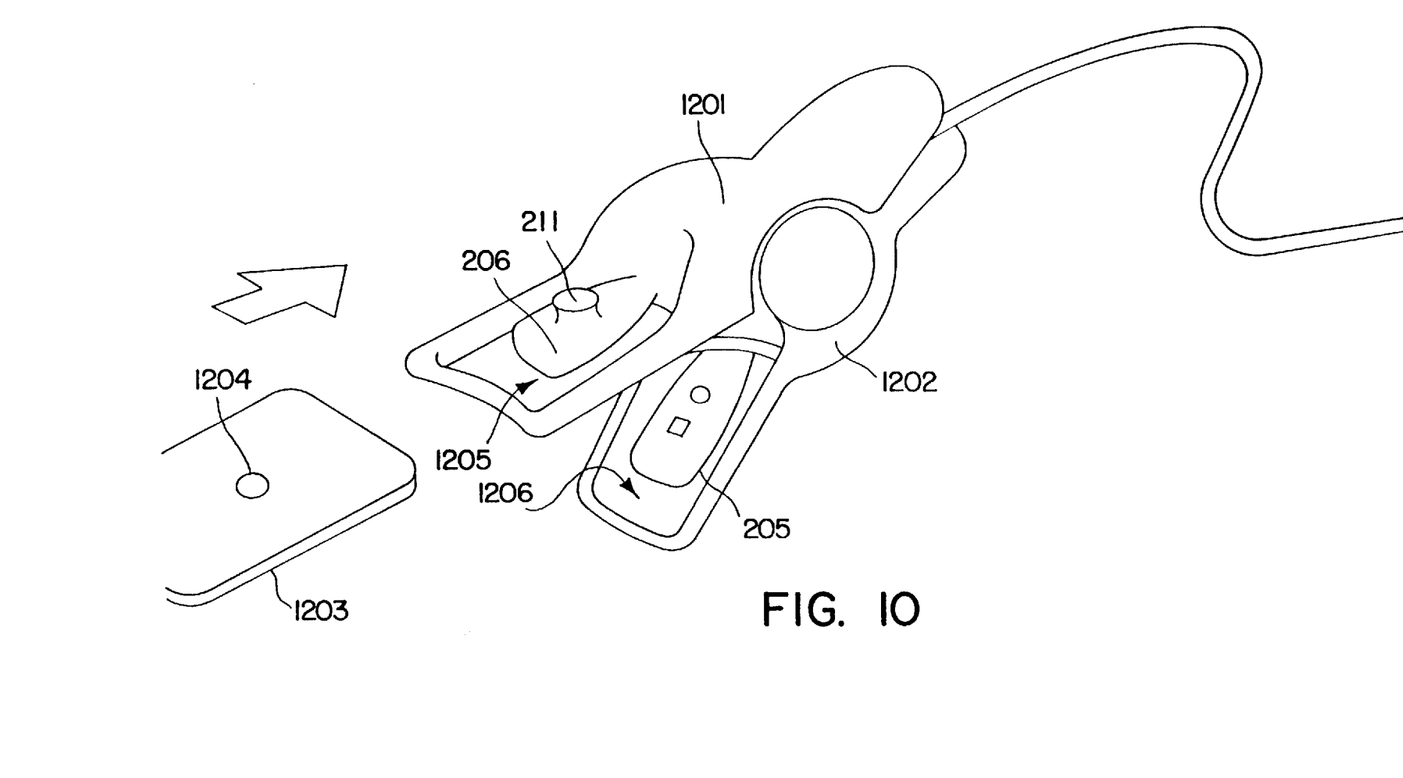
FIG. 10 is a diagram illustrating a sensor accessory that permits the sensor heads to pivot.

FIG. 10 illustrates yet another type of sensor accessory that facilitates tissue-sensor conformance by allowing the detector and transmitter to pivot. An upper (lower) clip piece 1201 (1202) defines a void 1205 (1206) in which detector 206 (transmitter 205) is positioned. Button shaped portion 211 of detector 206 is fitted through a hole 1204 inside a sleeve 1203 covering the part of upper clip piece 1201 defining void 1205. (In other embodiments, sleeve 1203 has a structure for mounting button portion 211, other than hole 1204, for example a button shaped pocket.) Detector 206 is thereby secured in position and still free to pivot within void 1205 about button shaped portion 211. Transmitter 205 is similarly secured in position. The upper and lower clip pieces of the accessory of FIG. 10 may contain features similar to those described above with reference to the accessory of FIG. 2 for limiting the degrees to which voids 1205 and 1206 can be brought together and separated, respectively.

Figure 11A:
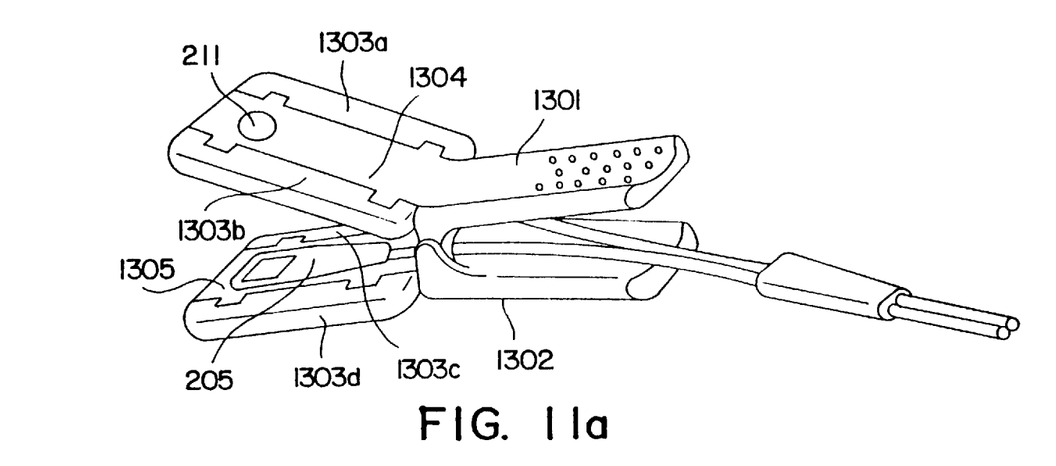
FIG. 11a is a diagram illustrating a sensor accessory with folding light shields.
Figure 11B:
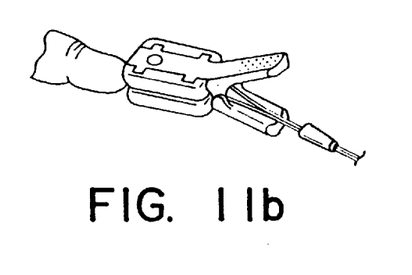
FIG. 11b is a diagram illustrating the sensor accessory of FIG. 11a applied to a non-flat site.

Another aspect of the present invention will now be discussed, in particular sensory accessories providing light shields that reduce shunting for non-flat site applications and yet do not interfere with sensor-tissue conformance in flat site applications. FIGS. 11a–b illustrate a sensory accessory 1300 suitable for application to both flat sites (such as the web between the thumb and forefinger) and non-flat sites (such as a finger). A sensory accessory 1300 contains upper and lower frames 1301 and 1302, respectively, which in one embodiment are made of polycarbonate. Button-shaped portion 211 of detector 206 and button-shaped portion of transmitter (not shown) are pushed through respective holes in portions 1304 and 1305 of upper and lower frames 1301 and 1302, thereby fixing in position detector 206 and transmitter 205 in respective pockets in portions 1304 and 1305. (In other embodiments, portions 1304–1305 have a structure for mounting the button shaped portion of a sensor head, other than a hole, for example a button shaped pocket.) Light shields 1303a–b & 1303c–d flank portions 1304 and 1305, respectively, and can be in an unrotated position in which light shields 1303a–b & 1303c–d are coplanar with portions 1304 and 1305 (as shown in FIG. 11a), suitable for flat site application, or can be rotated downward and upward, respectively (as shown in FIG. 11b where accessory 1300 is applied to a non-flat site).

Figure 12:
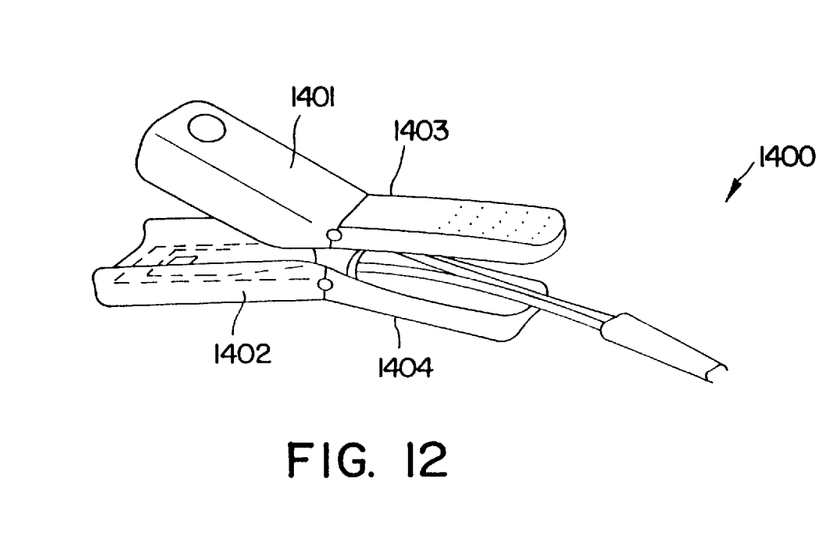
FIG. 12 is a diagram illustrating a sensor accessory with rubber sleeves having sides that act as light shields on flat sites and flatten under pressure on non-flat sites.

FIG. 12 illustrates a sensory accessory 1400 similar to that of FIG. 11a–b, with the rotatable light shields 1303a–d replaced with rubber sleeves 1401 and 1402, which cover portion 1304 of upper frame 1301 and portion 1305 of lower frame 1302, respectively. (In alternate embodiments, sleeves 1401 and 1402 could be made of a flexible material other than rubber.) Rubber sleeve 1401 (1402) has two sides that extend downward (upward) from portion 1304 (1305) and thereby reduce the amount of light shunted to detector 206 from transmitter 205 when sensory accessory 1400 is applied to non-flat sites. The sides of sleeves 1401 and 1402 flatten under the pressure of the grip of accessory 1400 on a flat site to become coplanar with portions 1304 and 1305. Thus, accessory 1400 is suitable for both flat and non-flat tissue sites.

Figures 13A, 13B, 13C:
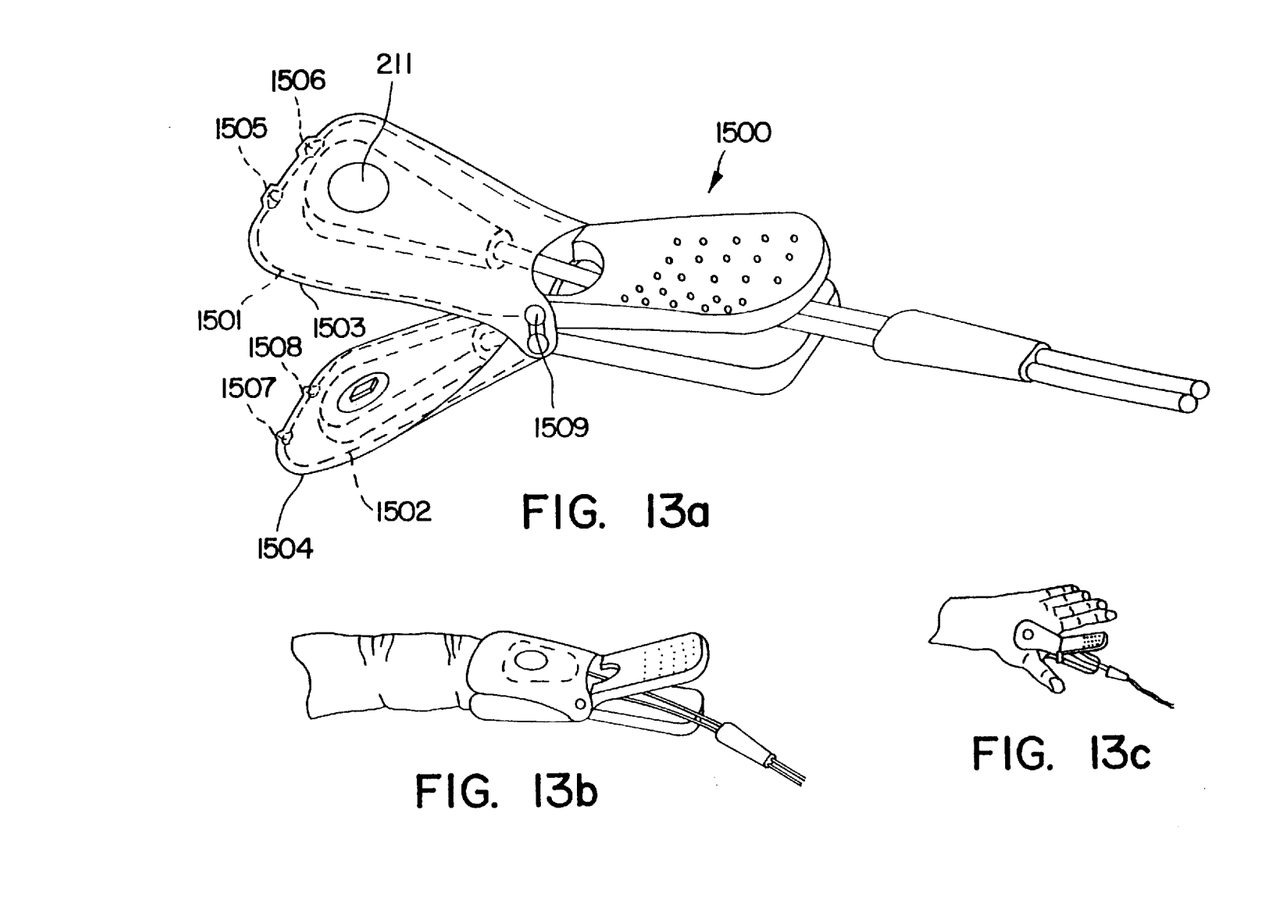
FIG. 13a is a diagram illustrating a sensor accessory with wire frames that can fold to surround a non-flat site.
FIG. 13b is a diagram illustrating the sensor accessory of FIG. 13a applied to a non-flat site.
FIG. 13c is a diagram illustrating the sensor accessory of FIG. 13a applied to a flat site.

FIGS. 13a–c illustrate a sensory accessory 1500 similar to that of FIG. 11a–b, with the rotatable light shields 1303a–d and the portions 1304 and 1305 of upper and lower frames 1301 and 1302, respectively, replaced with wire frames 1501 and 1502. Wire frames 1501 and 1502 each surround a void in which a respective one of the sensor heads is positioned. Rubber sleeves 1503 and 1504 cover wire frames 1501 and 1502, respectively. (In alternate embodiments, sleeves 1503 and 1504 could be made of a flexible material other than rubber.) The button shaped portion of each sensor head is fitted through a hole in a respective one of sleeves 1503–1504, thereby securing each sensor head in position but allowing each sensor head to pivot within a respective one of the voids about the sensor's button shaped portion. (In other embodiments, sleeves 1503–1504 have a structure for mounting the button shaped portion of a sensor head, other than a hole, for example a button shaped pocket.) Sleeves 1503 and 1504 are attached to the rest of accessory 1500 at one or more hinge/attachment pins 1509.

Wire frames 1501 and 1502 are spring loaded such that the spring force tends to bring together frames 1501 and 1502, which thereby grip patient tissue and conform to the tissue by folding at hinge points 1505–1508 to surround a non-flat tissue. The resulting folded sides of sleeves 1501 and 1502 serve as light shields as shown in FIG. 13b. Wire frames 1501 and 1502 do not fold at internal hinge/break points 1505–1508 when accessory 1500 is applied to a web site, as illustrated in FIG. 13c. Thus, accessory 1500 is also suitable for both flat and non-flat tissue sites. In other embodiments, means other than hinge points 1505–1508 for facilitating the folding of wire frames around a non-flat tissue site can be employed such as:

a) A connection, made of an elastomeric material (e.g. epdm or silicone rubber) or an elastic thermoplastic (e.g. polypropylene), could replace the portion of wire frames 1501 (1502) between the locations of hinge points 1505–1506 (1507–1508) in the above embodiment b) The portion of wire frames 1501 (1502) between the locations of hinge points 1505–1506 (1507–1508) in the above embodiment could be annealed and drawn thinner.

In one embodiment, hinge points 1505–1508 could be spring loaded so as to bias frames 1501 and 1502 in a folded position. Frames 1501 and 1502 would flatten under the pressure of the grip of accessory 1500 on a flat site.

While the above is a complete description of the preferred embodiments of the invention, various alternatives, modifications, and equivalents may be used. (For example, frames 1501–1502 of accessory 1500 (FIG. 13a) could be made of a glass-reinforced thermoplastic material instead of wire.) Therefore, the above description should not be taken as limiting the scope of the invention which is defined by the appended claims.

What is claimed is:

1. A sensor which electrooptically measures characteristics of blood in a patient's tissue comprising:

a first sensor head having a light emitter;

a second sensor head having a light detector;

a first support having a mount for removably press-fit mounting said first sensor head;

a second support having a mount for removably press-fit mounting said second sensor head, such that said light emitter is opposite said light detector;

said first and second supports defining first and second voids, respectively, said voids allowing said sensor heads to pivot about said mounts while said sensor is attached to a patient;

means for coupling said first and second supports together and biasing said mounts toward each other;

wherein said first and second supports and said means for coupling and biasing include a spring, the spring comprising:

first and second spring coils; and first and second spring frames defining the first and second voids, respectively, wherein the first and second spring frames are connected to both the first and second coils, and have an end shaped to fit a portion of the first and second sensor heads, respectively.

2. A sensor which electrooptically measures characteristics of blood in a patient's tissue comprising:

a first sensor head having a light emitter;

a second sensor head having a light detector;

a first support having a mount for removably press-fit mounting said first sensor head;

a second support having a mount for removably press-fit mounting said second sensor head, such that said light emitter is opposite said light detector;

said first and second supports defining first and second voids, respectively, said voids allowing said sensor heads to pivot about said mounts while said sensor is attached to a patient;

means for coupling said first and second supports together and biasing said mounts toward each other; and first and second removable sleeves for protecting the first and second sensor heads, respectively, from contaminants when mounted on said supports;

wherein the sleeves are largely opaque to light transmitted by the sensor, and thereby reduce the amount of light that travels from one of the sensor heads to the other without passing through the patient's tissue, said sleeves allowing transmission of light between said emitter and said detector.

3. The sensor of claim 2 wherein said sleeves have an opening over said sensor heads.

4. The sensor of claim 2 wherein said sleeves are substantially transparent over said sensor heads.

5. The sensor of claim 2, wherein the sleeves are made of a flexible material.

6. The sensor of claim 2, wherein the sleeves contain a portion contoured to conform to the patient's tissue.

* * * * *